(12) United States Patent
Haas et al.

(10) Patent No.: US 6,600,055 B2
(45) Date of Patent: Jul. 29, 2003

(54) PROCESS FOR THE EPOXIDATION OF OLEFINS

(75) Inventors: Thomas Haas, Frankfurt (DE); Willi Hofen, Rodenbach (DE); Jörg Sauer, Mobile, AL (US); Georg Thiele, Hanau (DE)

(73) Assignees: Degussa AG, Düsseldorf (DE); Uhde GmbH, Dortmund (DE)

( * ) Notice: Subject to any disclaimer, the term of this patent is extended or adjusted under 35 U.S.C. 154(b) by 0 days.

(21) Appl. No.: 10/170,233

(22) Filed: Jun. 13, 2002

(65) Prior Publication Data

US 2003/0009041 A1 Jan. 9, 2003

Related U.S. Application Data

(60) Provisional application No. 60/297,508, filed on Jun. 13, 2001.

(51) Int. Cl.$^7$ .............................................. C07D 301/12
(52) U.S. Cl. ........................................ 549/531; 549/523
(58) Field of Search ................................ 549/531, 523

(56) References Cited

U.S. PATENT DOCUMENTS

| | | | |
|---|---|---|---|
| 2,870,171 A | 1/1959 | Gable | |
| 4,410,501 A | 10/1983 | Taramasso et al. | |
| 4,833,260 A | 5/1989 | Neri et al. | |
| 5,523,426 A | 6/1996 | Jubin, Jr. et al. | |
| 5,591,875 A | 1/1997 | Chang et al. | |
| 5,599,955 A | 2/1997 | Vora et al. | |
| 5,620,935 A | 4/1997 | Thiele | |
| 5,675,026 A | 10/1997 | Thiele | |
| 5,760,253 A | 6/1998 | Danner et al. | |
| 5,849,937 A | 12/1998 | Jubin, Jr. et al. | |
| 5,849,938 A | 12/1998 | Reuter et al. | |
| 5,912,367 A | 6/1999 | Chang | |
| 6,042,807 A | 3/2000 | Faraj | |
| 6,063,941 A | 5/2000 | Gilbeau | |
| 6,372,924 B2 | 4/2002 | Thiele | |

FOREIGN PATENT DOCUMENTS

| | | |
|---|---|---|
| DE | 196 23 611 | 12/1997 |
| DE | 197 23 950 | 12/1998 |
| DE | 197 54 185 | 2/1999 |
| DE | 198 35 907 | 2/2000 |
| EP | 0 100 118 | 2/1984 |
| EP | 0 100 119 A1 | 2/1984 |
| EP | 0 106 671 A2 | 4/1984 |
| EP | 0 230 349 | 7/1987 |
| EP | 0 230 949 | 8/1987 |
| EP | 0 568 336 | 11/1993 |
| EP | 0 568 337 | 11/1993 |
| EP | 0 583 828 | 2/1994 |
| EP | 0 645 473 | 3/1995 |
| EP | 0 659 473 A1 | 6/1995 |
| EP | 0 712 852 A1 | 5/1996 |
| EP | 0 719 768 | 7/1996 |
| EP | 0 757 045 A1 | 2/1997 |
| EP | 0 795 537 | 9/1997 |
| EP | 0 827 765 | 3/1998 |
| EP | 0 930 308 A1 | 7/1999 |
| EP | 936 219 | 8/1999 |
| EP | 1 066 711 | 12/1999 |
| EP | 1 122 248 | 8/2001 |
| EP | 1 138 387 | 10/2001 |
| EP | 1 221 442 | 7/2002 |
| JP | 2166636 | 6/1990 |
| WO | WO 97/47613 | 12/1997 |
| WO | WO 97/47614 | 12/1997 |
| WO | WO 99/01445 | 1/1999 |
| WO | WO 99/07690 | 2/1999 |
| WO | WO 99/11639 | 3/1999 |
| WO | WO 00/07695 | 2/2000 |
| WO | WO 00/17178 | 3/2000 |

OTHER PUBLICATIONS

European Search Report, dated Jul. 10, 2001, 3 pps.

*Primary Examiner*—Ba K. Trinh
(74) *Attorney, Agent, or Firm*—Smith, Gambrell & Russell, LLP

(57) ABSTRACT

A process for the catalytic epoxidation of olefins with hydrogen peroxide in a continuous flow reaction system, wherein the reaction mixture is passed through a fixed catalyst bed within a reactor equipped with cooling means while maintaining a temperature profile within the reactor such that the cooling medium temperature of the cooling means is at least 40° C. and the maximum temperature within the catalyst bed is 60° C. at most.

26 Claims, No Drawings

PROCESS FOR THE EPOXIDATION OF OLEFINS

REFERENCE TO RELATED APPLICATION

This application claims the benefit of provisional application Ser. No. 60/297,508 filed Jun. 13, 2001 which is relied on and incorporated herein by reference.

INTRODUCTION AND BACKGROUND

The present invention relates to catalytic epoxidation of olefins with hydrogen peroxide in a continuous flow reaction system.

From EP-A 100 119 it is known that propene can be converted by hydrogen peroxide into propene oxide if a titanium-containing zeolite is used as catalyst.

Unreacted hydrogen peroxide cannot be recovered economically from the epoxidation reaction mixture. Furthermore, unreacted hydrogen peroxide involves additional effort and expenditure in the working up of the reaction mixture. The epoxidation of propene is therefore preferably carried out with an excess of propene and up to a high hydrogen peroxide conversion. In order to achieve a high hydrogen peroxide conversion it is advantageous to use a continuous flow reaction system. Such a reaction system may comprise either one or more tubular flow reactors or an arrangement of two or more flow mixing reactors connected in series. Examples of flow mixing reactors are stirred tank reactors, recycle reactors, fluidized bed reactors and fixed bed reactors with recycling of the liquid phase.

Furthermore the epoxidation of olefins with hydroperoxides is like most oxidation reactions highly exothermic. Thus precautions have to be taken to ensure sufficient removal of the heat generated by the exothermic reaction in order to control the reaction. This problem is especially pronounced in continuous flow systems using fixed bed reactors. Moreover conversion and product selectivity in epoxidation reactions with the effect that efficient temperature control is of uppermost importance.

According to a considerable number of patent disclosures as exemplified by EP-A 230 349, EP-A568 336, EP-A 712 852, EP-A 757 045, JP-A 2-166636, WO 97/47613 and U.S. Pat. No. 5,591,875 the epoxidation reaction of olefins with hydrogen peroxide is performed in a slurry of titanium containing zeolites as catalyst. In this reaction mode temperature control is less difficult and thus a wide range of suitable reaction temperatures from −20° C. to 150° C. are reported in these documents where in the examples temperatures between 0° C. and 85° C. were used.

EP-A 100 119 discloses in addition to reaction in a catalyst slurry the use of a tubular continuous flow reactor with a fixed catalyst bed that is immersed in a cooling bath thermostated at 15° to 20° C.

In WO 97/47614 in example 8 reaction of propene with hydrogen peroxide using a fixed bed tubular reactor having a cooling jacket is described. The temperature of the cooling medium is controlled by a thermostat to be in the range between 0°–5° C. Yield and product selectivity are still insufficient for commercial purposes.

As far as the applicants are aware all of the prior art documents referring to epoxidation of olefins with hydrogen peroxide in tubular fixed bed reactors equipped with cooling means disclose only the temperature of the cooling medium without providing any information with respect to the actual temperature within the reactor. As is known for example from Walter Brötz et.al., Technische Chemie I, Weinheim, 1982, pp 283; the temperature profile with respect to the cross-section of a tubular reactor is parabolic with increasing temperature from the periphery to the center of the reactor in case of exothermic reactions. Additionally the temperature may vary along the axis of the tubular reactor.

EP-A 659 473 describes an epoxidation process wherein a liquid mixture of hydrogen peroxide, solvent and propene is led over a succession of fixed bed reaction zones connected in series in down-flow operation. No temperature control means are present within the reactor to remove the generated heat from the single reaction zones. Thus each reaction zone can be considered as an independent adiabatic reactor. In each reaction zone the reaction is performed to a partial conversion, the liquid reaction mixture is removed from each reaction zone, is led over an external heat exchanger to extract the heat of reaction, and the major proportion of this liquid phase is then recycled to this reaction zone and a minor proportion of the liquid phase is passed to the next zone. At the same time gaseous propene is fed in together with the liquid feed stock mixture, is guided in a parallel stream to the liquid phase over the fixed bed reaction zones, and is extracted at the end of the reaction system in addition to the liquid reaction mixture as an oxygen-containing waste gas stream. Although this reaction procedure enables the propene oxide yield to be raised compared to conventional tubular reactors without the temperature control described in EP-A 659 473, it nevertheless involves considerable additional costs on account of the complexity of the reaction system required to carry out the process.

From U.S. Pat. No. 5,849,937 a process for epoxidation of propene using hydroperoxides especially organic hydroperoxides is known. The reaction mixture is fed to a cascade of serially connected fixed bed reactors in down-flow regime with respect to each single reactor. Similarly to the teaching of EP-A 659 473 in each reactor only partial conversion is accomplished and the reactors are not equipped with heat exchange means. Like in EP-A 659 473 the reaction heat is removed by passing the effluent from each reactor through heat exchangers prior to introducing the reaction mixture to the next fixed bed reactor in series thereby adding to the complexity of the reaction system.

The disadvantages of the reaction systems as discussed in EP-A 659 473 and U.S. Pat. No. 5,849,937 are the complexity and thus the increased costs for investment.

U.S. Pat. No. 5,599,955 refers to an epoxidation reaction in a fixed bed reactor whereby it is evident from example 1 that the reaction mixture is contacted with the titanium silicate catalyst in a temperature range between 40° C. to 60° C. But nevertheless, this reference does not disclose the cooling medium temperature of the cooling means.

In view of the cited prior art an object of the present invention is to provide a process for the epoxidation of olefines that results in improved conversion and product selectivity compared to WO 97/47614 which can be carried out using conventional reaction systems.

SUMMARY OF THE INVENTION

The above and other objects of the present invention can be achieved by a process for the catalytic epoxidation of olefins with hydrogen peroxide in a continuous flow reaction system, wherein the reaction mixture is passed through a fixed catalyst bed within a reactor equipped with cooling means while maintaining a temperature profile within the reactor such that the cooling medium temperature of the cooling means is at least 40° C. and the maximum temperature within the catalyst bed is 60° C. at most.

The present inventors have surprisingly discovered that by conducting the epoxidation reaction in such a way to fulfill the inventive temperature profile requirement an optimized balance between conversion and selectivity can be achieved with a standard reaction system. Thus, a process for epoxidation of olefins with high hydrogen peroxide conversion and product selectivity at low investment costs is available thereby improving the overall economics of the process. Due to the considerably high activation temperature for the epoxidation reaction the process has to be conducted at a certain minimum temperature to achieve economically reasonable conversion. But on the other hand the heat generated by the exothermic reaction has to be effectively removed from the reactor since at increased temperatures unwanted side reactions take place with the result that product selectivity is decreased. While maintaining the temperature profile in the reactor within the inventive very narrow range both goals could be simultaneously achieved.

EP-A-659 473 discloses that in conventional tubular reactors temperature rise in the catalyst bed exceeds 15° C. whereas according to the examples in EP-A-659 473 the temperature rise is 8° C. at most and in the preferred embodiment only 5½° C. Thus according to the teaching of EP-A-659 473 temperature rise within the catalyst bed has to be kept as low as possible in order to achieve high yields of propylene oxide. This reduced temperature rise could only be achieved according to EP-A-659 473 by conducting the reaction in a single reaction zone to only a partial conversion with the result that the majority of the reaction mixture has to be recycled, and by intermediate cooling the reaction mixture.

But contrary to this expectation, as will be shown in more detail below in the examples better overall yields based on hydrogen peroxide comparable to the most preferred embodiments in EP-A-659 473 are obtainable although a conventional reactor system without intermediate external cooling is used according to the present invention.

DETAILED DESCRIPTION OF THE INVENTION

In the practice of the present invention any reactor having a fixed catalyst bed and cooling means can be used. Preferably, tubular, multi-tubular or multi-plate reactors are used. Most preferably, tubular reactors having a cooling jacket are applied since they are standardly available at relatively low cost. As cooling medium that is pumped through the cooling means, preferably the cooling jacket, all standard cooling media like oils, alcohols, liquid salts or water can be used. Water is most preferred.

According to the present invention the temperature profile within the reactor is maintained such that the cooling medium temperature of the cooling means of the tubular reactor is at least 40° C. and the maximum temperature within the catalyst bed is 60° C. at most, preferably 55° C. By preference the temperature of the cooling medium is controlled by a thermostat.

The maximum temperature within the catalyst bed is measured with a plurality of suitable temperature measurement means like thermocouples or Pt-100 arranged approximately along the axis of the preferably tubular reactor in suitable distances with respect to each other. In this way the number, position within the reactor and distances between the temperature measurement means are adjusted to measure the temperature of the catalyst bed within the entire reactor as exact as necessary.

The maximum temperature of the catalyst bed can be adjusted by different means. Depending on the selected reactor type the maximum temperature of the catalyst bed can be adjusted by controlling the flow rate of the reaction mixture passing through the reactor, by controlling the flow rate of the cooling medium passing through the cooling means or by lowering the catalyst activity, for instance by diluting the catalyst with inert material.

The flow rate of the cooling medium is preferably adjusted to keep the temperature difference between entry of the cooling medium into the cooling means and exit below 5° C., preferably below 3° C., most preferably 2° C.

According to another preferred embodiment the reaction mixture is passed through the catalyst bed with a superficial velocity from 1 to 100 m/h, preferably 5 to 50 m/h, most preferred 5 to 30 m/h. The superficial velocity is defined as the ratio of volume flow rate/cross section of the catalyst bed. Consequently the superficial velocity can be varied in a given tubular reactor by adjusting the flow rate of the reaction mixture.

Additionally it is preferred to pass the reaction mixture through the catalyst bed with a liquid hourly space velocity (LHSV) from 1 to 20 $h^{-1}$, preferably 1.3 to 15 $h^{-1}$.

The process of the present invention can be conducted in down-flow or up-flow operation mode, whereby down-flow operation mode is more preferred. In a preferred embodiment of the present invention the process is conducted to maintain the catalyst bed in a trickle bed state.

Contrary to the teaching of EP-A 659 473 conducting conversion within a single reactor or reaction zone to a limited extent is not required and also not preferred according to the present invention. But in order to be able to operate the process continuously when changing and/or regenerating the epoxidation catalyst, two or more tubular flow reactors may if desired also be operated in parallel or in series in the before-described manner.

Crystalline, titanium-containing zeolites especially those of the composition $(TiO_2)_x(SiO_2)_{1-x}$ where x is from 0.001 to 0.05 and having a MFI or MEL crystalline structure, known as titanium silicalite-1 and titanium silicalite-2, are suitable as catalysts for the epoxidation process according to the invention. Such catalysts may be produced for example according to the process described in U.S. Pat. No. 4,410,501. The titanium silicalite catalyst may be employed as a shaped catalyst in the form of granules, extrudates or shaped bodies. For the forming process the catalyst may contain 1 to 99% of a binder or carrier material, all binders and carrier materials being suitable that do not react with hydrogen peroxide or with the epoxide under the reaction conditions employed for the epoxidation. Extrudates with a diameter of 1 to 5 mm are preferably used as fixed bed catalysts.

When practicing the present invention it is preferred that the overall feed stream to the reactor comprises an aqueous hydrogen peroxide solution, an olefin and an organic solvent. In this way, these components may be introduced into the reactor as independent feeds or one or more of these feeds are mixed prior to introduction into the reactor. The feed stream(s) to the reactor is (are) preferably adjusted to a temperature that differs from the temperature of the cooling medium by less than $X°$ C., preferably to a temperature that is about the same.

Using the process according to the invention any olefin can be epoxidized in particular olefin with 2 to 6 carbon atoms. The process according to the invention is most particularly suitable for the epoxidation of propene to propene oxide. For economic reasons it would be preferred for an industrial scale process to use propene not in a pure form but as a technical mixture with propane that as a rule contains 1 to 15 vol. % of propane. Propene may be fed as a liquid as well as in gaseous form into the reaction system.

The hydrogen peroxide is used in the process according to the invention in the form of an aqueous solution with a hydrogen peroxide content of 1 to 90 wt. %, preferably 10 to 70 wt. % and particularly preferably 30 to 50 wt. %. The hydrogen peroxide may be used in the form of the commercially available, stabilized solutions. Also suitable are unstabilized, aqueous hydrogen peroxide solutions such as are obtained in the anthraquinone process for producing hydrogen peroxide.

The reaction is preferably carried out in the presence of a solvent in order to increase the solubility of the olefin, preferably propene, in the liquid phase. Suitable as solvent are all solvents that are not oxidized or are oxidized only to a slight extent by hydrogen peroxide under the chosen reaction conditions, and that dissolve in an amount of more than 10 wt. % in water. Preferred are solvents that are completely miscible with water. Suitable solvents include alcohols such as methanol, ethanol or tert.-butanol; glycols such as for example ethylene glycol, 1,2-propanediol or 1,3-propanediol; cyclic ethers such as for example tetrahydrofuran, dioxane or propylene oxide; glycol ethers such as for example ethylene glycol monomethyl ether, ethylene glycol monoethyl ether, ethylene glycol monobutyl ether or propylene glycol monomethyl ether, and ketones such as for example acetone or 2-butanone. Methanol is particularly preferably used as solvent.

The pressure within the reactor is usually maintained at 5 to 50 bar, preferably at 15 to 25 bar.

The olefin is preferably employed in excess relative to the hydrogen peroxide in order to achieve a significant consumption of hydrogen peroxide, the molar ratio of olefin, preferably propene, to hydrogen peroxide preferably being chosen in the range from 1.1 to 10. When adding a solvent the amount of solvent is preferably chosen so that only a liquid phase is present in the reaction mixture. The solvent is preferably added in a weight ratio of 0.5 to 20 relative to the amount of hydrogen peroxide solution used. The amount of catalyst employed may be varied within wide limits and is preferably chosen so that a hydrogen peroxide consumption of more than 90%, preferably more than 95%, is achieved within 1 minute to 5 hours under the employed reaction conditions.

The present invention relates to a process for the catalytic epoxidation of olefins with hydrogen peroxide in a continuous flow reaction system, wherein the reaction mixture is passed through a fixed catalyst bed within a reactor equipped with cooling means while maintaining a temperature profile within the reactor such that the cooling medium temperature of the cooling means is at least 40° C. and the maximum temperature within the catalyst bed is 60° C. at the most.

It has been determined that certain reaction conditions are preferred for purposes of the invention. These are as follows:

a) the temperature profile within the reactor is maintained such that the maximum temperature within the catalyst bed is 55° C. at the most;

b) the reactor is a tubular reactor and the cooling means is a cooling jacket;

c) the reaction mixture is passed through the catalyst bed in down-flow operation mode;

d) the fixed catalyst bed is maintained in a trickle bed state;

e) the reaction mixture is passed through the catalyst bed with a superficial velocity from 1 to 100 m/h, preferably 5 to 50 m/h, most preferably 5 to 30 m/h;

f) the reaction mixture is passed through the catalyst bed with a liquid hourly space velocity (LHSV) from 1 to 20 $h^{-1}$, preferably 1.3 to 15 $h^{-1}$;

g) the pressure within the reactor is maintained at 5 to 50 bar, preferably at 15 to 25 bar;

h) a titanium-containing zeolite is used as catalyst;

i) the overall feed stream to the reactor comprises an aqueous hydrogen peroxide solution, an olefin and an organic solvent;

j) the organic solvent is methanol; and k) the olefin is propene;

The present invention will be explained in more detail referring to the following examples:

EXAMPLES 1 and 2

Comparative Examples 1–6

A titanium-silicate catalyst was employed in all examples. The titanium-silicate powder was shaped into 2 mm extrudates using a silica sol as binder in accordance with example 5 in EP 00 106 671.1. The $H_2O_2$ employed was prepared according to the anthrachinone process as a 40 wt-% aqueous solution.

Epoxidation is carried out continuously in a reaction tube of 300 ml volume, a diameter of 10 mm and a length of 4 m. The equipment is furthermore comprised of three containers for liquids and relevant pumps and a liquid separating vessel. The three containers for liquids comprised methanol, the 40% $H_2O_2$ and propene. The 40% $H_2O_2$ was adjusted with ammonia to a pH of 4.5. The reaction temperature is controlled via an aqueous cooling liquid circulating in a cooling jacket whereby the cooling liquid temperature is controlled by a thermostat. The reactor pressure was 25 bar absolute. Mass flow of the feeding pumps was adjusted to result in a propene feed concentration of 21.5 wt-%, a methanol feed concentration of 57 wt-% and an $H_2O_2$ feed concentration of 9.4 wt-%. The reactor was operated in down-flow operation mode.

When performing the examples and comparative examples the cooling jacket temperature ($T_{cool}$) and the total mass flow were varied and the maximum Temperature ($T_{max}$) measured as indicated in Table 1. The flow rate was adjusted to achieve comparable conversions. Product output was determined by gas chromatography and the $H_2O_2$ conversion by titration. On the basis of the gas chromatographical analysis of the hydrocarbons the selectivity was calculated. It results from the amount of propene oxide formed relative to the amount formed of all oxygen containing hydrocarbons.

TABLE 1

| No. | $T_{cool}$ [° C.] | $T_{max}$ [° C.] | Flow Rate kg/h | $H_2O_2$ Conversion [%] | Propene Oxide Selectivity [%] |
|---|---|---|---|---|---|
| CE1 | 30 | 40 | 0.35 | 71 | 98 |
| CE2 | 30 | 35 | 0.7 | 45 | 99 |
| E1 | 41 | 59 | 0.35 | 96 | 96 |
| E2 | 41 | 51 | 0.7 | 79 | 98 |
| CE3 | 49 | 78 | 0.7 | 90 | 91 |
| CE4 | 49 | 67 | 1.4 | 80 | 93 |
| CE5 | 61 | 81 | 2.8 | 74 | 91 |

The data as given in Table 1 demonstrate that an optimized balance of conversion and product selectivity is achieved within the narrow limits of cooling medium temperature and maximum temperature in the catalyst bed as defined by the present invention.

Further variations and modifications will be apparent to those skilled in the art from the foregoing and are intended to be encompassed by the claims appended hereto.

We claim:

1. A process for the catalytic epoxidation of an olefin with hydrogen peroxide in a reaction mixture in a continuous flow reaction system comprising passing the reaction mixture through a fixed catalyst bed within a reactor equipped with cooling means while maintaining a temperature profile within the reactor such that a cooling medium temperature of the cooling means is at least 40° C. and a maximum temperature within the catalyst bed is 60° C. at most to thereby react said olefin with said hydrogen peroxide.

2. The process of claim 1, wherein the temperature profile within the reactor is maintained such that the maximum temperature within the catalyst bed is 55° C. at most.

3. The process of claim 1, wherein the reactor is a tubular reactor and the cooling means is a cooling jacket.

4. The process of claim 2, wherein the reactor is a tubular reactor and the cooling means is a cooling jacket.

5. The process of claim 1, wherein the reaction mixture is passed through the catalyst bed in down-flow operation mode.

6. The process of claim 2, wherein the reaction mixture is passed through the catalyst bed in down-flow operation mode.

7. The process of claim 3, wherein the reaction mixture is passed through the catalyst bed in down-flow operation mode.

8. The process of claim 1, wherein the fixed catalyst bed is maintained in a trickle bed state.

9. The process of claim 2, wherein the fixed catalyst bed is maintained in a trickle bed state.

10. The process of claim 3, wherein the fixed catalyst bed is maintained in a trickle bed state.

11. The process of claim 5, wherein the fixed catalyst bed is maintained in a trickle bed state.

12. The process of claim 1, wherein the reaction mixture is passed through the catalyst bed with a superficial velocity from 1 to 100 m/h.

13. The process of claim 1, wherein the reaction mixture is passed through the catalyst bed with a superficial velocity from 5 to 50 m/h.

14. The process of claim 1, wherein the reaction mixture is passed through the catalyst bed with a superficial velocity from 5 to 30 m/h.

15. The process of claim 1, wherein the reaction mixture is passed through the catalyst bed with a liquid hourly space velocity (LHSV) from 1 to 20 $h^{-1}$.

16. The process of claim 1, wherein the reaction mixture is passed through the catalyst bed with a liquid hourly space velocity (LHSV) from 1.3 to 15 $h^{-1}$.

17. The process of claim 2, wherein the reaction mixture is passed through the catalyst bed with a liquid hourly space velocity (LHSV) from 1 to 20 $h^{-1}$.

18. The process of claim 3, wherein the reaction mixture is passed through the catalyst bed with a liquid hourly space velocity (LHSV) from 1 to 20 $h^{-1}$.

19. The process of claim 5, wherein the reaction mixture is passed through the catalyst bed with a liquid hourly space velocity (LHSV) from 1 to 20 $h^{-1}$.

20. The process of claim 12, wherein the reaction mixture is passed through the catalyst bed with a liquid hourly space velocity (LHSV) from 1 to 20 $h^{-1}$.

21. The process of claim 1, wherein pressure within the reactor is maintained at 50 to 50 bar.

22. The process of claim 1, wherein pressure within the reactor is maintained at 15 to 25 bar.

23. The process of claim 1, wherein a titanium-containing zeolite is the catalyst.

24. The process of claim 1, wherein a feed stream comprising an aqueous hydrogen peroxide solution, an olefin and an organic solvent is fed to the reactor as the overall feed stream.

25. The process of claim 24, wherein the organic solvent is methanol.

26. The process of claim 1, wherein the olefin is propene.

* * * * *